United States Patent [19]

Thomas

[11] 4,108,849

[45] Aug. 22, 1978

[54] PROCESS FOR EXTRACTING AND PROCESSING GLYCOPROTEINS, MUCOPOLYSACCHARIDES AND ACCOMPANYING SUBSTANCES

[76] Inventor: André Thomas, 8, rue Pierre et Marie Curie, 75005 Paris, France

[21] Appl. No.: 552,061

[22] Filed: Feb. 24, 1975

[30] Foreign Application Priority Data

Feb. 25, 1974 [FR] France .................. 74 06369
Aug. 8, 1974 [FR] France .................. 74 27513
Feb. 11, 1975 [FR] France .................. 75 04148

[51] Int. Cl.$^2$ ........................... A23J 1/20
[52] U.S. Cl. .................. 260/122; 260/112 R; 424/95; 424/104; 424/105; 424/195
[58] Field of Search .................. 260/112 R, 121, 122; 424/95, 104, 105

[56] References Cited

U.S. PATENT DOCUMENTS

| | | | |
|---|---|---|---|
| 2,595,459 | 5/1952 | Hull .................. | 260/122 |
| 3,404,142 | 10/1968 | Shank et al. .................. | 260/112 R |
| 3,522,229 | 7/1970 | Yamamoto et al. .................. | 260/112 R |
| 3,644,326 | 2/1972 | Pien .................. | 260/112 R X |

*Primary Examiner*—Walter C. Danison
*Attorney, Agent, or Firm*—Ostrolenk, Faber, Gerb & Soffen

[57] ABSTRACT

The extraction and processing of glycoproteins and/or mucopolysaccharides and accompanying substances, from natural substances, such as tissues of animal, cryptogamic, bacterial or other plant organisms, or materials produced by such organisms is disclosed. The substance is treated with water of buffers with a pH value of 7.5 to 9.5, in one or more stages, at between atmospheric temperature and 110° C. The precipitated solids are separated out, while the unprocessed extract is clarified and stabilized, and possibly mixed with fatty substances, obtained, for example, from extracts of organs containing complex lipids in a natural state of equilibrium. These new, very stable extracts are particularly suitable for aqueous, fatty or dry mixtures, for industrial, medical or cosmetic purposes. One important application involves the preparation of an extract of lactoserum, in liquid, paste or powder form, which is very stable, soluble, and will not precipitate in the presence of heat. Extracts can undergo a final re-sterilization process after packaging.

13 Claims, No Drawings

PROCESS FOR EXTRACTING AND PROCESSING GLYCOPROTEINS, MUCOPOLYSACCHARIDES AND ACCOMPANYING SUBSTANCES

This invention relates to a new process for extracting and preparing extracts of any animal or human organs or tissues and cells, or any plants or micro-organisms, or liquids of biological origin, such as serums, amniotic liquids, secretions, reactive liquids and tissues, liquids produced by various cultures, containing glycoproteinic and mucopolysaccharidic substances, and those forming them (proteins, mucins, chondroids, or their derivatives, such as mucoitin-sulphuric acid, mucoitin, mucosin, glucosamine, chondroitin-sulphuric acid, chondroitins, chondrosamine, and glycuronic acid), or which can be combined with them naturally (viscous polymers such as hyaluronic acid and its compounds, glycuronic acid and N-acetylglucosamine), as well as nucleoproteins or their component substances, and other proteins, glucoproteins, mucopolysaccharides, lipoproteins, glycolipoids glucids, etc.

These processes have been developed after a large number of comparative tests, and they allow such biological extracts to be obtained on an industrial scale, in a more or less viscous, stable and micro-biologically sterile form. Biological extracts obtained in this way can be used, or combined with one another, mixed with suitable vehicles. They can also be combined with other substances possessing therapeutic properties, which they help the skin to absorb. Finally, they can be lyophilized and later completely dissolved.

The invention also covers the new stable total extracts obtained by this process, the conditions for combining of such extracts with one another, specially recommended compositions and combinations of these extracts with suitable excipients, or combination with products, or lyophilization with the possibility of complete dissolving.

In general, advantage is taken of the known fact that certain proteins, glycoproteins, mucopolysaccharides and accompanying substances are, depending on conditions, particularly those concerning the ionic state, pH-value, etc, heat-resistant, and will remain in solution. Such heat resistance concerns an alkaline or approximately neutral medium. Heating applied under clearly defined conditions can, simultaneously with extraction, produce micro-biological sterility. However, such sterility can also be obtained, in a codified way, and according to this invention, by effective chemical agents, possibly self-destructible. In this new process, the organ or micro-organisms are ground down in water or a medium containing a low level of electrolytes (or directly, if a liquid of biological origin is used as raw material), and an initial extraction is performed in a basic medium. pH-values of between 7.5 and 9.5, and preferably between 8 and 9, are used. Extraction, by light hydrolysis of the suspension, or extraction of the liquid, is allowed to continue for an adequate time, at atmospheric temperature, or in an oven, after which is it heated in an autoclave to 110° C, leaving it to decant at atmospheric temperature, and then separate out the deposit that is formed, centrifugally or by filtration.

The original aspect of this invention is the use of an aqueous buffer solution with a pH-value of more than 7, whereas the sensitivity of proteinic compounds to alkalinity is well-known, and almost neutral media are used in the prior art (for example the extraction of mucin as described by Ward Pigman, in "Exposés Annuels de Biochimie Médicale", 1963, pp. 67–84). The advantage of working in a basic medium accordingly constitutes an unexpected feature of this invention, which comprises the pH-value limitations mentioned above.

The pH-value of the untreated extract depends on the organ involved, and the value of the extraction liquid has to be adapted to suit it.

The liquid used for extraction is water or a buffer solution, preferably of a sodium-phosphate desoxycholate type, or tris (hydroxymethyl) aminomethane, N-tris (hydroxymethyl) methylglycine, or any other buffer solution normally used in biology (see Handbook of Biochemistry, C.R.C., p. J.238).

The extraction operation falls into two parts, one being performed at atmospheric or fairly low temperature, and the other at high temperature, approximately 100° to 110° C. A special feature of the invention is that this operation can be performed in one or more stages, each at one temperature or a sequence of temperatures, between atmospheric temperature and 110° C. For example, the first part can be performed at between 15° and 60° C, and then in one or more stages at between 60° and 110° C. In one recommended embodiment, initial extraction is performed at between 15° and 45° C while during the subsequent stage or stages, the temperature is 80° to 110° C. Lower temperatures are preferably used with the highest pH-values.

The time taken for extraction naturally depends on the nature and the concentration of the raw material involved, on pH-value, and on temperature. The criterion, at each stage, is the production of a significant amount of glycoproteins and/or mucopolysaccharides, dissolving of which can be followed by analysis.

Any residue left after centrifugation can be re-extracted by adding water, and the suspension, raised to a new pH-value of 8 to 9, can be heated and re-centrifuged to produce fresh extract.

In general, extracts contain proteinic compounds, often in relatively large amounts, as indicated below. They are not precipitated by heat, but by acids (in particular trichloracetic acid), alcohol, acetone, etc, and contain soluble glycoproteids, which produce the typical purplish-red colour with the hydrochloric solution of p-dimethylaminobenzaldehyde.

The process can be used to produce extracts of organs with fairly high concentrations, of approximately 30%. They are opaque, and more or less adhesive. They are then diluted before use, to concentrations of 5 to 10%. They can be clarified and stabilized simultaneously, for example by means of a mixture of a surface-active sterilized substance, such as sodium lauryl-sulphate or another product with the same effect, and/or mixed solvents, polyoxyethylene ethers and phenoxypolyethoxyethanols, added in amounts that will ensure a low concentration, approximately 0.5 to 1% of the final product. Finally, extracts are totally clarified and stabilized. They remain sterile, do not give off any unpleasant odour, are penetrating, non-adhesive, and smooth in consistency.

These extracts can be used for medical and cosmetic purposes. When they are combined with cosmetic preparations, they tend to improve or activate them, by providing the skin with cellular glycoproteins and mucopolysaccharids, mainly of foetal origin. It has recently been discovered that certain glycoproteins are almost entirely foetal in origin, and have a considerable physiological effect on cells and tissues.

The substances can also be used as excipients or additives for medical preparations or physiological purposes.

Total extracts obtained by this process are suitable for lyophilization. It should be noted that such lyophilisates will dissolve in very small quantities of aqueous solvents, so that they can be mixed with fatty substances. Brief stirring will then immediately produce an emulsion, liquid or solid depending on the relative concentrations involved, and in which the concentrated aqueous phase, mainly of glycoproteinic and mucopolysaccharidic form, is suspended in the fatty phase. This preparation is extremely smooth, and is very easily absorbed by the skin. This means that the mixture can be prepared when required, in individual doses, for instance, or be stored and remain stable.

One particular feature of this invention is that the extracts of organs can be enriched with complex lipoids, extracted from other organs containing large amounts of such substances, such as proteo- and glycolipoids, phosphatides, sphingolipoids, cerebrosides, gangliosides and even sterols. These can be obtained by heating suitable organs, in an alkaline medium, in a state of natural equilibrium. Extracts obtained from foetal brains or the white bone-marrow of young animals are particularly recommended, though many others can also be used. Some lipoids separate out, particularly at low temperatures, but a lipo-proteinic emulsion remains, which can be added to the extracts of organs obtained by this new process. The mixture is found to be stable and translucent, and it increases the smoothness, and lubricating and penetrating properties of the extracts. These properties are further improved when the solution of extracts of organs contains penetrating agents, such as sodium desoxycholate.

The penetrating capacity can be assessed by a simple test. Extracts are coupled with peroxidase, and spread on the skin. Extracts marked in this way can be detected, histologically, as far as the lower layers of the cutis, after several applications to the skin. They are also found to accumulate in growing zones with high metabolism.

One specially useful application of the process is the production of stable lactoserum extract, in liquid, paste or powder form. This liquid, or the aqueous solution prepared from the paste or powder, offers the advantage of being able to re-form a milky-white aqueous suspension, and of not precipitating in the presence of heat.

The first stage in the preparation of lactoserum is the standard one of precipitating the milk casein by some existing method, namely by adding acid or enzyme. According to this new method, however, it is better to perform precipitation using rennet, using a method known per se. The whey is separated from the casein and alkalinized to the pH-value referred to above, and heated for a short period, usually a few minutes, at the temperature referred to above. Heat-sensitive proteins precipitate during cooling. They are separated out and the liquid, which constitutes the lactoserum extract, is collected, and concentrated, preferably at not more than 60° C, possibly in a vacuum. However, it can be dried or prepared in powder form by atomization. This produces a thick liquid, paste or powder, depending on the method used.

It should be noted that this process eliminates denatured heat-sensitive proteins, which form a kind of superfluous ballast during various processes performed on the untreated lactoserum, such as atomization, and even desalinization by inverse osmosis, electrodialysis, and so on. The quantity of such proteins is fairly low, but they interfere when they precipitate, and need to be removed. If they are not removed, the untreated lactoserum, atomized directly, forms a powder containing insoluble denatured substances, which are deposited in the water and produce a yellow scum.

This new process offers two other innovations. Heat-sensitive proteins can be removed immediately after heating of the alkaline lactoserum, by centrifugation when hot or by filtration, without the need to wait. This greatly simplifies installations and operations.

In addition, non-toxic soluble substances, suitable for human consumption in the amounts indicated, and which perform a protective, stabilizing role, can be added to the hot lactoserum extract as soon as the heat-sensitive substances have precipitated, and before concentration or atomization operations are performed. These mixtures, which protect and stabilize the lactoserum during drying, without reducing its solubility, may be carboxyvinylic polymers with a high molecular weight, or other non-toxic water-soluble polymers, possibly mixed with small amounts of non-toxic, water soluble surface-active substances.

For example, small amounts of mixtures of 0.5% carboxyvinylic polymers in water can be added to the lactoserum before atomization, to produce this protective effect.

The heat-resistant lactoserum extract obtained by this process, and which is in liquid, concentrate or powder form, is suitable for use in foodstuffs, as an industrial, pharmaceutical or cosmetic raw material, in culture media for yeasts, or with protein-producing microorganisms or other products.

Extracts prepared in this way, and which have been clarified, stabilized and sterilized, can provide active preparations, or be used as excipients or additives for medicinal substances with known properties. For example, they can act as excellent protective and penetrating vehicles for substances affecting pigmentation, such dihydroxyacetone, salicylic or paraaminobenzoic esters, or sodium urocanate. Dihydroxyacetone reacts with the amino acids of extracts, such as placenta or skin extracts, regularizing its reaction in vivo, and making it more physiological and homogeneous. The reaction can also be intensified by enriching the extracts with certain amino acids, such as arginine.

When these extracts are used as excipients for drugs, absorption per os is improved and the effect of general reactions widened. In addition, the permeative effect through cutaneous absorption is considerably increased.

These various stable, sterile biological extracts, prepared as described in the examples below, can be used separately in varying concentrations, or combined with one another in various ways, dissolved or mixed with various excipients, or lyophilized.

When mixed with suitable excipients, the extracts provide solutions, suspensions, or gels of varying fluidity, translucent or opaque, creamy-white or reddish, smooth in texture and neutral, and which will not produce any reaction or irritation on the skin, for example, even after long use, which will penetrate quickly, and soften and hydrate the teguments.

Such extracts, which may be neutralized with carbon dioxide, can be dessicated or frozen, and lyophilized. However, there is a particular problem in lyophilizing them, since they are heat-resistant proteinic compounds, which have accordingly been heated to 110° C, and which have to be protected from further denaturating effects. The solvents in which they are re-dissolved should also resemble the original solutions, as regards viscosity, penetrating capacity, etc. Even after dessication in a blower at 80° C, for example, this can be achieved, but results obtained by lyophilization are much better.

Without adding protective substances, lyophilizates may contain a small amount of fairly denatured material, which dissolves slowly. One feature of the invention is the choice of the protective substances to be added to such extracts before lyophilization, substances that will themselves be lyophilizable, and not cause any harmful effect, and in the choice of the dissolving mixtures for the lyophilizates obtained. Several substances used under such conditions cannot be employed, because they affect the properties of the extracts to some degree. This applies to sodium ricinoleate, for example, which would otherwise give excellent lyophilizates.

Suitable substances for addition include sodium laurylsulphate, in suitable proportions and in various combinations. The dissolving mixture can also contain a buffer system, and possibly permeating agents, in non-denaturing amounts, such as sodium desoxycholate. The addition of salivary extract or lactoserum extract obtained by the process provide excellent solvents, which supplement the properties of the lyophilizate.

Extracts, even those containing large amounts of glycoproteins and mucopolysaccharides, such as umbilical cord, mucous membranes, skin, brain, placenta, cartilages, and the liquids referred to, once lyophilized, are re-dissolved immediately and completely in a small amount of suitable solvent. These concentrated solutions retain the respective physiological properties of the initial extracts.

Percutaneous administration of extracts, with fast resorption, helps to provide teguments with biological, foetal and other factors thus prepared. But when they are provided in a neutral solution, or after lyophilization, they are easier to apply by the digestive tract.

Extracts obtained by this process can be used separately, or combined with one another, with or without excipients, and divided into human extracts on the one hand, such as extract of umbilical cord jelly, placenta extract, and human haemoserum extract, and on the other hand, animal or plant extracts, such as extract of mucous membranes, skin, placenta, brain, cartilage, bone marrow, and various cells, or lactoserum, saliva extract, haemoserum extract, amniotic liquids, or reactive liquids, or extracts of micro-organisms, various cultures, yeast, seaweed, fungus, seed extracts, and so on. In such combinations can be made by preparing extracts after mixing the raw materials, and possibly concentration.

One general, very significant feature of the invention is that all these extracts are heat-resistant, and that whether combined or not with other suitable substances, they can be subjected to final re-sterilization in the autoclave, after final prcessing, whatever form this takes.

In addition to the general properties thus described, these bacteriologically sterile extracts and preparations reveal special properties when spread on the skin, producing a beneficial effect on zones that are irritated, erythematous or inflamed, slightly burnt, or which have undergone certain dermatological reactions.

The effect of the preparations can be strengthened in several ways, since they can be mixed with substances of known effect, without destroying their stability, causing them to separate out, or reducing their viscosity significantly, if presented in the form of solution or gel; such substances can also be added before the lyophilization.

The following examples will illustrate the invention, although it is not confined to them. Examples 1 to 7 are intended to show the extraction of the preparation process, using various types of raw materials, involving human or animal organs, lyophilizates, liquids from living organisms, notably lactoserum, but the process is of course a general one, and applies to any other organs, liquids or products of organisms.

EXAMPLE 1

Extraction from human or animal umbilical cord

The umbilical cord is known to contain a special natural jelly of high viscosity (Warton jelly in the case of human cord), with important protective properties. It consists mainly of mucoproteins, hyaluronic acid, and unequal amounts of other accompanying substances, proteins, lipoids and glucids. The relative viscosity of the sodium salt in hyaluronic acid is also known to be considerably affected by the presence of electrolytes, and this is used in preparing extracts.

Healthy human umbilical cords, for example, collected in non-sterile conditions, are washed with jets of water. The blood from their vessels is removed, by being pressed out under water at high pressure, from one end to the other, in a cylinder machine, for example. They are cut up or chopped into pieces and washed again. The remaining haemoglobin is bleached by brief submersion in hydrogen peroxide. The pieces are then drained vigorously. They are creamy-white in colour.

Research shows that the average weight of each cord, for a sufficient number, is approximately 17 to 18 gr. Extraction is done with distilled water or by 0.26%-tris sodium desoxycholate buffer solution, using a ratio of weight of tissue to weight of extraction liquid to uit the purpose sought.

The suspension of fragments of cord is ground fine by a high-speed grinder, for example a "Polytron" grinder or "Colloidal" continuous grinder or some other model. The pH-value of the resulting ground material is adjusted to 8, using normal caustic soda. The viscosity then increases considerably, producing an opaque white gluey substance. Extraction continues for approximately 2 hours, at 37° C.

The preparation is then heated in an autoclave, either to 100° C in a flow of steam, or to 110° C, for an amount of time that depends on the amount involved. It is left to cool and decant at atmospheric temperature, for approximately 24 hours. This operation, which in fact amounts to a second extraction, results in an increase in the amount of dissolved or suspended proteinic substances, as analysis shows. The liquid is then centrifuged or filtered.

Residues can be re-extracted in water. The suspension is realkalinized, up to a pH-value of 9, then heated in the autoclave to 110° C, allowing a denatured residue and floating layer to be separated out by centrifugation or filtering. This liquid re-extracted from the residues is very opalescent. It can be added to the main extract or used separately.

The resulting extract is pale yellow, translucent, of moderate opalescence, and viscous. It has a pH-value of between 7 and 7.5. If the value is higher, and has to be adjusted, depending on the type of excipient which may subsequently be used, for example, this is done by bubbling carbon dioxide through, and not by adding HCl.

Biochemical analysis shows that such extracts contain mucoprotein and substances resulting from them or associated with them, and even after heating as described, proteins that can be analysed and detected by various tests, such as electrophoresis. Even after the method involving heating to 110° C, for example, proteinic substances, as assessed by the Lowry process, for example, can exceed 5 g $^o/_{oo}$. These heat-resistant extracts can be resterilized after final processing.

EXAMPLE 2

Extraction from human or animal placenta

Healthy placenta is washed in a jet of water. It may also be subjected to high-speed circulatory washing, using a trisodic citrate solution, for example, or even water. This washing is done through the first one and then the other of the two umbilical veins, using a syringe or washing bottle. Placentas are then cleaned of their membranes and largest conjunctive structures. When this has been done, the placental tissue is broken up and washed again in water, and then drained. Any haemoglobin in the fragments can be bleached, if necessary, by being dipped in hydrogen perioxide. Final draining is then done at high pressure.

Extraction can be done to the required concentration, using distilled water or, and this is preferable, a buffer solution of the 0.26%-tris sodium desoxycholate, adjusted to the necessary pH-value.

EXAMPLE 3

Use of lyophilized extracts, with instant preparation of an individual cream

A lyophilizate, corresponding to 2 ml extract of organs, prepared by means of this new process, is dissolved in 1 ml sterile solvent in a flask, consisting of a buffer with the lactoserum extract. The resulting concentrated solution is immediately emulsified by brief agitation by hand, in 10 ml sterile, fatty excipient, consisting of a mixture containing 80% polyoxyethylene ethers, 10% fatty alcohols, and 10% sweet almond oil. This immediately produces a quantity of cream, in which the biological extracts are dissolved and concentrated in the aqueous phase, itself emulsified in the fatty phase. This emulsion is a solid, homogeneous, white, extremely smooth, stable, sterile cosmetic preparation, which will not pick up infection in use. It is bacteriological sterile, and can be absorbed remarkably well by the skin, which it softens, moisturizes and lubricates simultaneously. If offers many cosmetic and health benefits.

EXAMPLE 4

Extraction from saliva

Mucin can be extracted from various mucigen-producing organs: the mucous membrane of the digestive system, saliva glands and other mucus-producing organs, even from invertebrates. In this case, the technique can be adapted from the process described above in connection with human umbilical cord.

The example of saliva is chosen, however, because it is extremely convenient, and offers a fairly plentiful source of material. The saliva is supplied by cattle, made to salivate by the known method of applying pilocarpin. This produces large amounts of saliva: for example, a bullock will produce several decalitres in 24 hours. This total saliva is mainly enriched with mucins by sublingual saliva. It is normally alkaline, with a pH-value of approximately 8.5.

The total saliva is immediately passed through a gauze filter, and placed directly in an autoclave, being heated to 110° C for a period of time depending on the amount involved. A thin layer of precipitate then adheres to the base of the containers. The product is stored cold, for 1 or 2 days, producing additional sedimentation of a small non-adhesive deposit. The liquid is then centrifugalized or filtered. It is limpid and viscous, with a pH-value of 8 or slightly more. The Lowry process is used to detect approximately 1 g $^o/_{oo}$ or slightly more protein. Electrophoresis detects at least two categories of protein. This sterile saliva extract, containing mucoproteins, is extremely stable in its existing form. It can be used in various preparations and combinations, and can withstand final re-sterilization after processing.

EXAMPLE 5

Lactoserum

Lactoserum is mainly produced from cow's milk by the usual method (skimming, acid or enzyme precipitation of the casein, straining, centrifugation or filtration). When lactoserum is sterilized by bacteriological filtration, it forms a limpid golden-yellow liquid, non-viscous and acid, with a pH-value of 4 or 5. It can contain 6 g $^o/_{oo}$ protein, as assessed by the Lowry process. After precipitating by heating, at acid pH, the protein content drops.

The main point of the invention is that if the lactoserum is first alkalinized to a pH-value of approximately 8, then heated in an autoclave to approximately 110° C, the resulting product will be different. This degree of hydrolysis produces, in addition to a precipitate, a pale orange-coloured liquid, the pH-value of which drops during heating to slightly under 7. After cooling and extraction periods, as described above, centrifugation separates out a residue and a pale orange-coloured, opalescent liquid, of remarkable stability, which will produce no further precipitation when heated, or any deposit, even over a long period. This liquid retains a fairly high level of proteinic substances, approximately 5.5 g $^o/_{oo}$ using the Lowry process: In other words, a level of concentration of proteinic substances fairly close to that of filtered, unheated acid lactoserum. Electrophorosis, performed on the liquid after heating, shows at least 2 types of protein.

This principle of preparation by controlled alkaline hydrolysis, with suitable heating, can also be applied to other liquids from organisms, such as human and animal haemoserum, amniotic liquid, reactive ascite liquid, or micro-organism cultures, bacteria, fungi, in particular yeasts. In these cases, the concentration of the extract can vary depending on the use to which it is to be put, and it can be re-sterilized in the autoclave after processing.

EXAMPLE 6

Dry concentrated lactoserum

Cow's milk is mixed with rennet, in the normal way, and the casein that precipitates after mixing is separated out by filtration or centrifugation. A small amount of concentrated caustic soda is added to the resulting whey to bring its pH-value to 8. The liquid is then heated to 80° C for 5 minutes. A white precipitate of denatured heat-sensitive proteins immediately forms, and this is separated out for possible use; this residue accounts for some 1% of the weight of liquid treated. Separation produces a lactoserum extract, pale yellow and slightly greenish in colour, opalescent, and with a pH-value of approximately 7.6, containing 5.5 g heat-resistant protein per liter. When subjected to concentration at 60° C, the liquid produces a creamy-white paste, or concentrated whey. In another preparation, the paste is dried until it becomes solid, and crushed by grinding or atomized to produce powder. A protective effect is obtained by adding small amounts of substances, such as mixtures of 0.5% carboxylic polymers in water. The resulting powder contains 10% weight of heat-resistant proteinic substances, approximately 75% total glucids (mainly hexoses, represented by lactose, accompanied by a small amount of other sugars, particularly glucose and lactose), 5 to 7% total lipoids and 6% mineral salts. Both the lactoserum paste and the matching powder keep well, and can easily be re-dissolved in water.

EXAMPLE 7

Jelly concentrates of lactoserum, enriched with nutritional materials

Processes for preparing lactoserum extracts can produce concentrated preparations in jelly form, enriched in various ways for food purposes.

In this case, the lactoserum is heated to approximately 80° C for about 10 minutes, which may be adequate, producing a concentration of 4 to 5.

This concentrate is mixed with a substance that causes gelling: gelose, alginates or others, such as a carrageen like Staiagel. The amount can be 0.6 to 0.8 g %. The preparation can be used in this form, or, depending on requirements, enriched with additives such as sugar, chocolate, vanilla, fruit juice or pulp or other flavours, or any other food preparation.

After processing, the products are sterilized in the autoclave to 110° C for 30 minutes. Before being place in the autoclave, preparations remain liquid, at the levels of gelling agent indicated, but after heating and re-cooling they become homogeneous jellies, yellow or of other colours, depending on the additives included, and they are sterile, stable, pleasent-tasting, and of definite nutritional value. On the other hand, if the thermolabile proteins have not been first removed, products are lumpy and unsatisfactory.

These lactoserum concentrates have a pH-value of apprximately 7, and contain 20 g or more heat-resistant proteins, approximately 5 g total lipids and 20 to 22% total ash per liter, for a concentration of 4 to 5. The level of mineral salts can be lowered if necessary, by treating with ion-exchanger resins, for example simply by mixing and stirring, or by any other process. The weight of total dried matter in the concentrate reaches nearly 300 g per liter.

What is claimed is:

1. In a process for extracting glycoproteins and mucopolysaccharides from animal or plant matter containing the same by extraction with aqueous medium, the improvement which comprises conducting the extraction at a pH between 7.5 and 9.5, heating said aqueous extract to a temperature of 100° to about 110° C, and without adding additional reagents separating precipitate from the aqueous extract and recovering the aqueous extract.

2. The process of claim 1 wherein said pH is between 8 and 9.

3. The process of claim 1 wherein said aqueous media is water or water buffered to said pH.

4. The process of claim 3 wherein said buffer is sodium desoxycholate phosphate, trishydroxymethylated aminomethane or methylglycin.

5. The process of claim 1 wherein said extraction is carried out for 1-12 hours and said heating is carried out for 0.25-3 hours.

6. The process of claim 1 wherein said matter extracted is an animal tissue.

7. The process of claim 1 wherein said matter extracted is plant tissue.

8. The process of claim 6 wherein said matter extracted is whey, said process yielding a stable lactoserum extract.

9. The process of claim 1 further comprising the step of sterilizing said aqueous extract after said separation of said precipitate.

10. The process of claim 1 wherein said pH is 8-9, and wherein said extraction is effected at a temperature of between 15° and 60° C.

11. In a method of producing a stable lactoserum extract by the extraction of whey with an aqueous medium, the improvement which comprises conducting said extraction at a pH of 7.5 to 9.5, heating the aqueous extract to a temperature of 100° to about 110° C. and without adding additional reagents separating precipitate from the aqueous extract and recovering the aqueous extract.

12. The method of claim 11 wherein the pH of the whey is adjusted to about 8 by adding an aqueous alkaline medium thereto, and the resulting mixture is heated to a temperature of about 110° C. whereby a precipitate of denatured heat sensitive protein forms.

13. Lactoserum produced by the process of claim 1.

* * * * *